United States Patent [19]

Knips

[11] 4,385,002
[45] May 24, 1983

[54] MONOARYL THALLIUM III PERCHLORATES AND THEIR PREPARATION

[75] Inventor: Ulrich Knips, Kamen-Heeren-Werve, Fed. Rep. of Germany

[73] Assignee: Rutgerswerke Aktiengesellschaft, Frankfurt am Main, Fed. Rep. of Germany

[21] Appl. No.: 282,378

[22] Filed: Jul. 13, 1981

[30] Foreign Application Priority Data

Aug. 9, 1980 [DE] Fed. Rep. of Germany ....... 3030273

[51] Int. Cl.³ .............................................. C07F 5/00
[52] U.S. Cl. .............................................. 260/429 R
[58] Field of Search ................................... 260/429 R

[56] References Cited

U.S. PATENT DOCUMENTS 4,122,106 10/1978 Brill ............................... 260/429 R
4,226,790 10/1980 Walker ........................... 260/429 R

OTHER PUBLICATIONS

Bull. Chem. Soc., Japan, vol. 44 (1971), p. 545.

Primary Examiner—Helen M. S. Sneed
Attorney, Agent, or Firm—Hammond & Littell, Weissenberger and Muserlian

[57] ABSTRACT

A process for the preparation of monoaryl thallium III perchlorates substantially free of isomers comprising reacting at atmospheric pressure at 0° to 80° C. thallium III perchlorate, 1 to 6 moles of a carboxylic acid, 1 to 6 moles of an aromatic compound and 2 to 15 moles of aqueous perchloric acid containing 3 to 45% by weight of water, said molar ratio being based on thallium III perchlorate and recovering the precipitated monoaryl thallium III perchlorate which are useful intermediates for the preparation of esters of aryl carboxylic acids.

12 Claims, 1 Drawing Figure

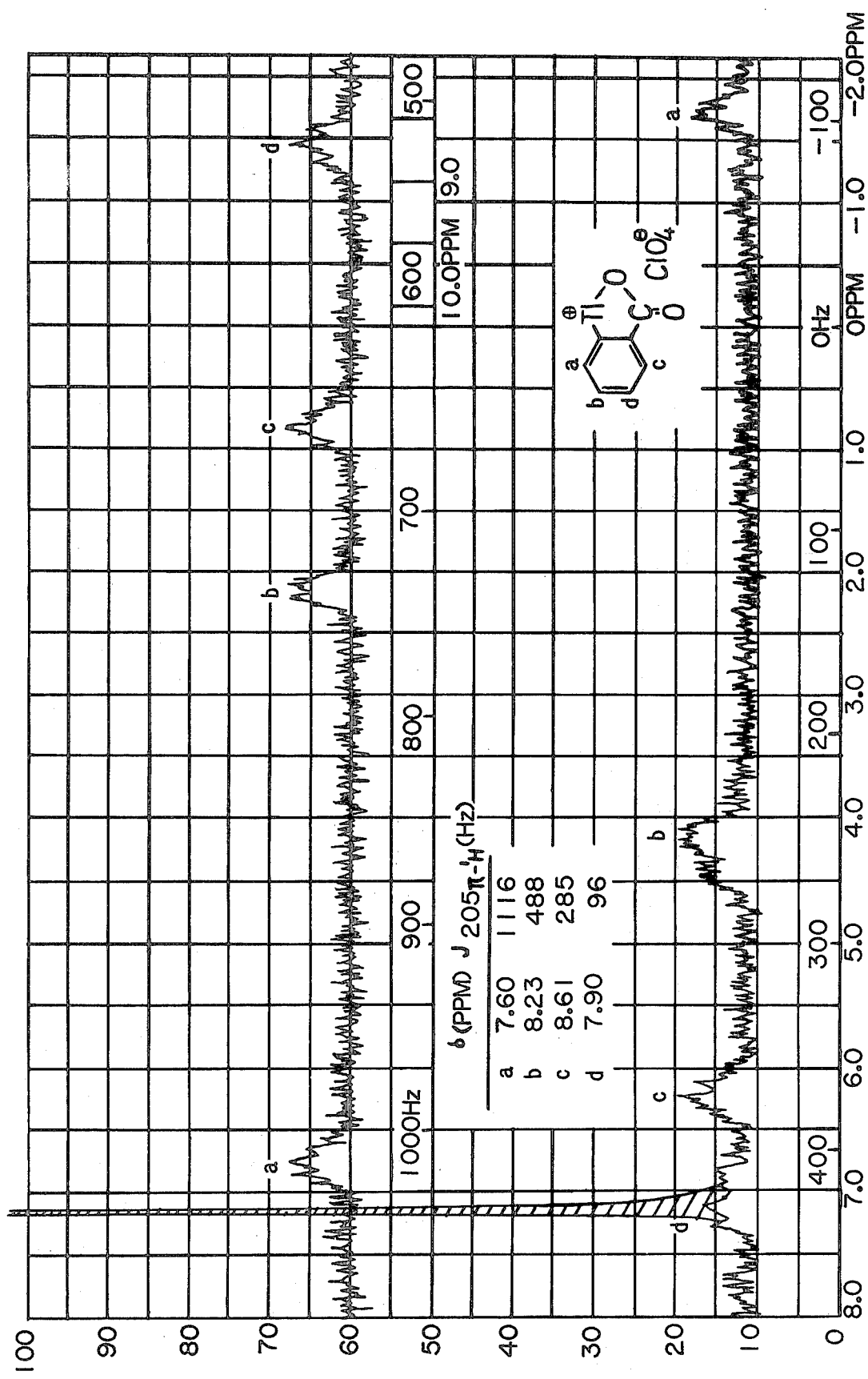

MONOARYL THALLIUM III PERCHLORATES AND THEIR PREPARATION

STATE OF THE ART

Bull. Chem. Soc. Japan, Vol. 44 (1971), p. 545 describes the preparation of monohydrates of monoaryl thallium acetate perchlorates having the formula

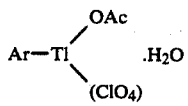

wherein Ac is acetyl and Ar is phenyl, tolyl, xylyl or anisyl by reacting equimolar amounts of Tl(OAc)$_3$ and perchloric acid in solution in acetic acid with an excess of the aromatic compounds. The amount of acetic acid is at least 20 molar excess with respect to the thallium salt.

For the reaction with toluene, the reaction was effected at 80° C. for 8½ hours and for reaction with benzene, the reaction was effected at 90° C. for 6 hours. Xylene was reacted at 110° C. for 2 hours and only with anisol could mild reaction conditions of 35° C. for one hour be used. The yields of aryl thallium salts given were 54.9% for benzene, 38.4% for p-xylene, 51.3% for m-xylene, 22.6% for p-xylene, 67% to 73.1% for toluene and 44% for anisol. However, in the experimental part of the report, substantially lower yields of the thallium salts were capable of being recovered and there were substantial amounts of byproducts produced. Moreover, the reaction conditions in the experimental description were different from the data in the listing of the yields and attempts to repeat the examples have shown that the high yield of products could not be obtained over with the corresponding conditions listed so the yields listed in the data probably reflect the amount of arylthallium salts capable of being detected in solution. Moreover, the dark color of the solution and the considerable formation of TlClO$_4$ observed as a result of decomposition reactions indicate that high isolated yields are not possible.

OBJECTS OF THE INVENTION

It is an object of the invention to provide a novel process for the preparation of monoaryl thallium III carboxylate perchlorate salts in high yields with short reaction times.

It is a further object of the invention to provide novel aryl thallium III carboxylate perchlorate salts.

It is another object of the invention to provide a process for the preparation of monoaryl thallium III carboxylate perchlorate salts under said conditions to substantially eliminate secondary reactions and obtain the salts substantially free of isomers.

These and other objects and advantages of the invention will become obvious from the following detailed description.

THE INVENTION

The novel process of the invention for the preparation of monoaryl thallium III perchlorates substantially free of isomers comprises reacting at atmospheric pressure at 0° to 80° C. thallium III perchlorate, 1 to 6 moles of a carboxylic acid, 1 to 6 moles of an aromatic compound and 2 to 15 moles of aqueous perchloric acid containing 3 to 45% by weight of water, said molar ratio being based on thallium III perchlorate and recovering the precipitated monoaryl thallium III perchlorate.

Thallium III perchlorate can be added to the reaction mixture in solid form or by dissolving Tl$_2$O$_3$ or suitable salts such as thallium III acetate in perchloric acid. Preferably, a solution of TlClO$_4$ or thallium I hydroxide or thallium I carboxylates in 55 to 70% perchloric acid is subjected to anodic oxidation to obtain a solution of thallium III perchlorate or Tl(ClO$_4$)$_3$ in perchloric acid. This latter method has the advantage that the thallium I salts obtained in all arylthallium salt reactions can be recycled without further treatment and the solution obtained after completion of the anodic oxidation is directly used for the thallation of the aromatic compound after addition of the carboxylic acid.

The arylthallium salts formed by the process precipitate from the reaction mixture at room temperature after a few minutes of reaction time which time can be extended by increasing the concentration of the carboxylic acid and/or water. When larger amounts of carboxylic acid or water than those indicated are used, the yield of arylthallium salts isolated are very poor or the reaction at room temperature may completely cease.

The precipitated thallium salts can be separated from the mother liquor by known methods and the mother liquor can be recycled to the reaction after addition of Tl(ClO$_4$)$_3$. Preferably, the mother liquor is admixed with TlClO$_4$ and the solution is subjected to anodic oxidation and after completion of the anodic oxidation, the solution is directly used in the reaction. The mother liquor should be substantially completely removed from the arylthallium salts as even small amounts of the mother liquor have an adverse effect when the said salts are used to prepare aryl carboxylic acid esters.

While the thallation reaction may be effected at 0° to 80° C., room temperature is preferred since the amount of isomers produced increases as the temperature increases. With aromatic compounds having an electrophilic substituent such as benzoic acid, reaction temperatures of 40° to 80° C., preferably 60° C., are used to obtain shorter reaction times.

The resulting thallium salts are more than 95% free of isomers without purification by crystallization and contain only small amounts of unreacted aromatic compounds, carboxylic acids or perchloric acid so that the salts need not be purified before reaction to form aromatic carboxylic acid esters or biaryl compounds. The yield of the recovered arylthallium salts is on the order of 80 to 90% which yields are increased if the mother liquors are recycled. The said salts have a purity of 90 to 95% and are substantially free of isomers but pure salts can be obtained, if desired, by crystallization from glacial acetic acid.

The carboxylic acid reactant may be an aliphatic carboxylic acid of 1 to 8 carbon atoms such as alkanoic acids like formic acid, acetic acid, n-propionic acid, n-butyric acid and isobutyric acid or aromatic carboxylic acids such as benzoic acid.

The aromatic reactant is preferably a monocyclic aromatic compound optionally substituted with at least one alkyl of 1 to 7 carbon atoms such as benzene, o-xylene, p-xylene, m-xylene, toluene, ethylbenzene, n-butylbenzene, sec-butylbenzene, isobutylbenzene and tert.butylbenzene.[1] If the aromatic reactant is solid at the reaction temperature, it may be dissolved in an inert organic solvent such as petroleum ether or cyclohexane.

(1) The reaction is not limited to monocyclic compounds since polycyclic systems e.g. indane do not fail to react.

Surprisingly, aromatic carboxylic acids may be used both as the aromatic reactant and as the carboxylic acid reactant so that a second carboxylic acid need not be added to the reaction except to enhance the solubility of the reactants.

The thallium salts perpared by ths process of the invention which are novel compounds have a chelate structure which is illustrated by the benzoic acid thallization product having the formula

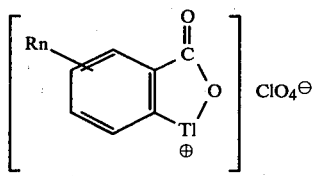

wherein R is alkyl of 1 to 7 carbon atoms and n is an integer from 0 to 3. The said structure has been determined by the NMR spectrum and an elemental analysis of corresponding hydroxides. The said arylthallium perchlorate salts are soluble in alcohol and are almost completely precipitated as the hydroxide when subjected to hydrolysis as seen from its elemental analysis. The resulting hydroxides are insoluble in organic solvents but can be dissolved in concentrated strong acids to obtain a plurality of salts of the complex arylthallium III carboxylate cations which have an amphoteric nature since they are also soluble in strong alkali metal hydroxide solutions.

The arylthallium salts of invention may be used to prepare aromatic carboxylic acid esters or biaryl compounds and for any known reaction monoarylthallium salts will undergo such as the preparation of aryl iodides.

The arylthallium III carboxylate-perchlorate of formula I may be reacted with water to form the corresponding arylthallium III carboxylate hydroxide of the formula

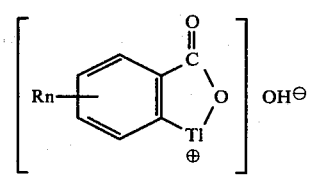

wherein R and n have the above definitions which can be used in the same way as the arylthallium III carboxylate perchlorate salts.

In the following examples, there are described several preferred embodiments to illustrate the invention. However, it is to be understood that the invention is not intended to be limited to the specific embodiments.

EXAMPLE 1

A solution of 507 g (1 mole) of thallium III perchlorate or $Tl(ClO_4)_3$, 60 g (one mole) of acetic acid and 560 g (3 moles) of 55% perchloric acid was vigorously stirred at room temperature with 100 g. (1.1 moles) of toluene and after a few minutes, a colorless precipitate of the hydrate of p-tolyl thallium acetate perchlorate began to form which could lead to a solidified reaction mixture if the stirring is inadequate. The solid salt was recovered by centrifugation and was then repeatedly washed with toluene and dried to obtain 425 g (90% yield) of the said colorless organothallium salt 98% free of isomers.

EXAMPLE 2

A suspension of 200 g (0.66 moles) of thallium I perchlorate or $TlClO_4$ in 500 g. (3 moles) of 60% perchloric acid was subjected to anodic oxidation to obtain a solution of about 0.6 moles of thallium III perchlorate which was reacted with 40 g (0.66 mols) of acetic acid and 60 g (0.66 moles) of toluene as described in Example 1 to obtain p-tolyl thallium acetate perchlorate.

EXAMPLES 3 TO 11

Using the procedure of Example 1, a solution of thallium III perchlorate in 55% perchloric acid was reacted with equimolar amounts of acetic acid and the aromatic hydrocarbons of Table I for 10 to 15 minutes and the yields and the products are reported in Table I.

TABLE I

| Example No. | Aromatic compound substance | % Yield | Aryl group of arylthallium acetate-perchlorate |
|---|---|---|---|
| 3 | Benzene | 83 | Phenyl- |
| 4 | o-Xylene | 85 | 3,4-Dimethylphenyl- |
| 5 | m-Xylene | 88 | 2,4-Dimethylphenyl-* |
| 6 | p-Xylene | 84 | 2,5-Dimethylphenyl- |
| 7 | Ethylbenzene | 81 | 4-Ethylphenyl- |
| 8 | n-Butylbenzene | 85 | 4-n-Butylphenyl- |
| 9 | sec.-Butylbenzene | 87 | 4-sec.Butylphenyl- |
| 10 | iso-Butylbenzene | 83 | 4-iso-Butylphenyl- |
| 11 | tert.-Butylbenzene | 81 | 4-tert.-Butylphenyl- |

*forms no hydrate.

EXAMPLES 12 TO 15

Using the procedure of Example 1, a solution of thallium III perchlorate in 55% perchloric acid was mixed with a equimolar amounts of a carboxylic acid of Table II and after addition with an equimolar amount of toluene, the salts of Table II were formed after 10 to 15 minutes.

TABLE II

| Example No. | Carboxylic Acid | % Yield | Final Product |
|---|---|---|---|
| 12 | Propionic acid | 83 | p-Tolylthalliumpropionate-perchlorate |
| 13 | formic acid | 81 | p-Tolylthalliumformiate-perchlorate |
| 14 | n-butyric acid | 85 | p-Tolylthalliumbutyrate-perchlorate |
| 15 | iso-butyric acid | 83 | p-Tolythalliumisobutyrate-perchlorate |

EXAMPLE 16

122 g of benzoic acid were added to a solution of 503 g of $Tl(ClO_4)_3$ and 60 g of acetic acid in 500 g of 55% perchloric acid, and the mixture was stirred vigorously for 5 hours at 60° C. After centrifuging off the precipitate, excess benzoic acid was extracted therefrom with ether, and the solid was taken up in ethanol to isolate small amounts of $TlClO_4$. After evaporating the solvent a 63% yield of complex 2-carboxyphenyl thallium III perchlorate free of isomers and benzoate (determined by NMR Spectrum) was obtained.

EXAMPLE 17

The solution of 2-carboxyphenyl thallium III perchlorate in ethanol of Example 16 was admixed with water and complete precipitation was avoided by addition of dilute sodium hydroxide solution. The mixture was washed with water and dried to obtain 205 g (60% yield) of 2-carboxyphenyl thallium III hydroxide.

Analysis: $C_7H_5O_3Tl$ Calculated: %C 24.62; %H 1.48; %O 14.06; %Tl 59.85. Found: %C 24.91; %H 1.64; %O 13.96; %Tl 59.19.

Various modifications of the process of the invention may be made without departing from the spirit or scope thereof and it should be understood that the invention is intended to be limited only as defined in the appended claims.

What I claim is:

1. A process for the preparation of monoaryl thallium III perchlorates substantially free of isomers comprising reacting at atmospheric pressure at 0° to 80° C. thallium III perchlorate, 1 to 6 moles of a carboxylic acid, 1 to 6 moles of an aromatic compound and 2 to 15 moles of aqueous perchloric acid containing 3 to 45% by weight of water, said molar ratio being based on thallium III perchlorate and recovering the precipitated monoaryl thallium perchlorate.

2. The process of claim 1 wherein the reaction temperature is room temperature.

3. The process of claim 1 or 2 wherein the thallium III perchlorate is formed by dissolving thallium oxide or a thallium salt in perchloric acid.

4. The process of claim 1 or 2 wherein the thallium III perchlorate is prepared by anodic oxidation of a perchloric acid solution of thallium I perchlorate, thallium I hydroxide or thallium I carboxylate wherein the carboxylic acid is an aliphatic carboxylic acid or aromatic carboxylic acid and the aromatic compound and carboxylic acid are added to the resulting solution.

5. The process of claim 1 or 2 wherein the aromatic reactant is a solid at the reaction temperature and is added as a solution in an inert organic solvent.

6. A compound of the formula

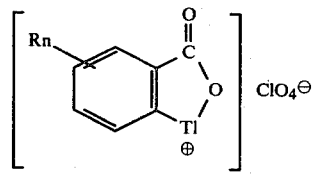

wherein R is alkyl of 1 to 7 carbon atoms and n is an integer from 0 to 3.

7. A process for the preparation of a compound of claim 6 comprising reacting at atmospheric pressure at temperatures of 40° to 80° C. thallium III perchlorate and an aromatic carboxylic acid of the formula

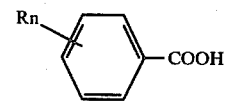

wherein R is alkyl of 1 to 7 carbon atoms and n is an integer from 0 to 3 in a molar ratio of 1:1 to 6 in 2 to 15 moles of 55 to 70% perchloric acid and recovering the compound of claim 6.

8. The process of claim 7 wherein the reaction temperature is about 60° C.

9. The process of claim 7 wherein the recovered product is dissolved in an organic solvent and is reacted with water to obtain the corresponding arylthallium III carboxylate hydroxide of the formula

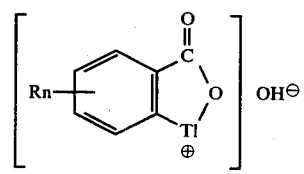

wherein R and n are defined in claim 7.

10. The process of claim 1 wherein the aromatic compound is selected from the group consisting of indane and monocyclic aromatic compounds optionally substituted with at least one alkyl of 1 to 7 carbon atoms.

11. The process of claim 1 wherein the aromatic compound is selected from the group consisting of benzene optionally substituted with at least one alkyl of 1 to 7 carbon atoms and benzoic acid.

12. The process of claim 1 or 10 wherein the carboxylic acid is selected from the group consisting of benzoic acid and alkanoic acids of 1 to 8 carbon atoms.

* * * * *